United States Patent
Lin

(10) Patent No.: US 11,214,877 B2
(45) Date of Patent: *Jan. 4, 2022

(54) GAS GENERATOR

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 357 days.

This patent is subject to a terminal disclaimer.

(21) Appl. No.: 16/386,548

(22) Filed: Apr. 17, 2019

(65) Prior Publication Data
US 2019/0242020 A1 Aug. 8, 2019

Related U.S. Application Data

(63) Continuation of application No. 15/639,365, filed on Jun. 30, 2017, now Pat. No. 10,301,726.

(30) Foreign Application Priority Data

Jun. 30, 2016 (TW) ................. 105120686

(51) Int. Cl.
*C25B 15/08* (2006.01)
*C25B 9/17* (2021.01)
(Continued)

(52) U.S. Cl.
CPC ............... *C25B 9/17* (2021.01); *A61M 16/10* (2013.01); *A61M 16/107* (2014.02);
(Continued)

(58) Field of Classification Search
CPC .. C25B 15/08; C25B 1/04; C25B 9/00; C25B 9/06; C25B 15/02; C25B 1/00; C25B 1/02; C25D 17/00; C25D 21/04
See application file for complete search history.

(56) References Cited

U.S. PATENT DOCUMENTS

| 5,720,789 A | 2/1998 | Pinson |
| 2013/0206586 A1 | 8/2013 | Lin |
| 2015/0190604 A1 | 7/2015 | Lin |

FOREIGN PATENT DOCUMENTS

| CN | 104661724 A | 5/2015 |
| DE | 202014004509 U1 | 10/2014 |

(Continued)

OTHER PUBLICATIONS

Chinese Office Action; Application No. 201710519343.2, dated Aug. 23, 2019, 6 pages.

(Continued)

*Primary Examiner* — Zulmariam Mendez
(74) *Attorney, Agent, or Firm* — Rosenberg, Klein & Lee

(57) ABSTRACT

The present invention provides a gas generator and comprises an electrolytic cell, a condensate filter device, and an atomizing device. The electrolytic cell is for electrolyzing electrolyzed water to generate a gas with hydrogen. The condensate filter device includes a gas pathway, a filter, and an isolated component. The isolated component is used for limiting the movement of the filter inside the gas pathway. The gas generated from the electrolytic cell is condensed and filtered through the filter for generating a filtered gas with hydrogen. The atomizing device is used for generating an atomizing gas to be mixed with the filtered gas to generate a healthy gas. The present invention uses the condensate filter device to filter out the electrolyte from the filtered gas with hydrogen to be mixed with the atomizing gas for generating the healthy gas.

12 Claims, 6 Drawing Sheets

(51) Int. Cl.
    *A61M 16/10*     (2006.01)
    *C25B 15/02*     (2021.01)
    *B01D 46/00*     (2006.01)
    *B01D 46/10*     (2006.01)
    *B01F 3/04*     (2006.01)
    *C25B 1/04*     (2021.01)
    *C02F 1/461*     (2006.01)

(52) U.S. Cl.
    CPC ......... *B01D 46/0019* (2013.01); *B01D 46/10* (2013.01); *B01F 3/04021* (2013.01); *C25B 1/04* (2013.01); *C25B 15/02* (2013.01); *C02F 1/4618* (2013.01); *Y02E 60/36* (2013.01)

(56) References Cited

FOREIGN PATENT DOCUMENTS

| | | | |
|---|---|---|---|
| EP | 3018103 | A2 | 11/2016 |
| JP | 50-111776 | U1 | 9/1975 |
| JP | 11-189890 | A | 7/1999 |
| JP | 2009-072755 | A | 12/2007 |
| JP | 2016-108657 | A | 6/2016 |
| JP | 2016108657 | A | 6/2016 |
| TW | 201615895 | A | 5/2016 |

OTHER PUBLICATIONS

European Office Action; Application No. 17178960.5, dated Nov. 8, 2017, 7 pages.

GAS GENERATOR

This application is a continuation of U.S. application Ser. No. 15/639,365, filed on Jun. 30, 2017 which is hereby incorporated by reference as if fully set forth herein.

BACKGROUND OF THE INVENTION

1. Field of the Invention

The present invention relates to a gas generator, and more particularly, the present invention relates to a gas generator with a function of filtering out an electrolyte in a gas generated from the gas generator.

2. Description of the Prior Art

People are always paying a great deal of attention on health developments. Many developments in medical technology are often targeted on treating diseases and prolonging human life. However, most of the treatments in the past are passive, which means that they only treat the disease when the disease occurs. These methods include operation, medication, radiation therapy, chronic diseases care, rehabilitation, corrective therapy, or even medical treatments for cancers. But in recent years, much of the research from medical experts are gradually moving towards preventive medical methods, such as research on healthy food, screening and preventing inherited diseases, which actively prevents diseases from occurring in the future. Because of the focus on prolonging human life, many anti-aging and anti-oxidation technologies including skin care products and anti-oxidation food/medicine are gradually being developed and are becoming increasingly popular to the general public.

Studies have found that there are instable oxygen species (O+), also known as free radicals, in the human body. The free radicals are usually generated due to diseases, diet, environment and one's lifestyle, but they can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are clinical experiments showing that patients who need to inhale a high concentration of oxygen for an extended period of time would experience lung damage and the lung damage, and they could be ameliorated by inhaling hydrogen.

However, the gas with hydrogen generated by electrolyzing electrolyzed water usually with high temperature and electrolyte. It is unsuitable for person to breathe directly. Additionally, if a user wants to breathe a healthy gas, the gas with hydrogen will need to be mixed with an atomizing gas or a volatile essential by another device for formed the healthy gas, thereby causing inconvenience in the use of the conventional electrolytic apparatus.

SUMMARY OF THE INVENTION

Therefore, the present invention is to provide a gas generator. Firstly, the gas generator electrolyzes liquid water to generate a gas with hydrogen. Then the gas generator condenses the gas with hydrogen and filters out electrolyte in the gas with hydrogen. After that, the gas generator mixes the gas with hydrogen with an atomizing gas to generate a healthy gas for a person to breathe suitably.

The present invention provides a gas generator comprising an electrolytic cell, a condensate filter device, and an atomizing device. The electrolytic cell contains electrolyzed water, wherein the electrolyzed water comprises an electrolyte. The electrolytic cell is used for electrolyzing the electrolyzed water to generate a gas with hydrogen. The condensate filter device comprises a gas pathway, a filter, and an isolated component. The gas pathway is used for receiving the gas with hydrogen. The filter is configured in the gas pathway for filtering the gas with hydrogen to generate a filtered gas with hydrogen. The isolated component is configured in the condensate filter device for limiting the movement of the filter in the gas pathway. The atomizing device is used for receiving the filtered gas with hydrogen, wherein the atomizing device further generates an atomizing gas to be mixed with the filtered gas with hydrogen to generate a healthy gas.

The isolated component can be an isolated cube or a pathway barrier sheet. The condensate filter device has an inlet and a vent, and the inlet and the vent are connected to the gas pathway respectively. The gas with hydrogen enters the gas pathway through the inlet. The vent is used for outputting the filtered gas with hydrogen. The isolated component is used for preventing the filter from flowing into the inlet or the vent by limiting the movement of the filter in the gas pathway. It should be understood that the word "limiting" of the present invention is not equal to "fixing", but reducing the degree of the filter movement. Wherein, the condensate filter device comprises a top cover of the gas pathway and a bottom cover of the gas pathway. The top cover of the gas pathway is configured on the bottom cover of the gas pathway, and the gas pathway is formed when the top cover of the gas pathway is combined with the bottom cover of the gas pathway.

Additionally, the bottom cover of the gas pathway comprises a pathway substrate, and the pathway barrier sheet is configured on the pathway substrate. The gas pathway meanderingly distributed over the condensate filter device is formed when the top cover of the gas pathway is combined with the bottom cover of the gas pathway. Furthermore, the pathway substrate and the isolated component are formed integrally by one process. Besides, the filter comprises a plurality of filter films, and each filter film is limited by the isolated component.

The gas generator of the present invention further comprises a humidification device connected between the condensate filter device and the atomizing device. The humidification device is used for further moisturizing and filtering the filtered gas with hydrogen received from the vent and outputting the filtered gas with hydrogen to the atomizing device.

To summarize the statement mentioned above, the priority of the present invention is to provide a gas generator. In the gas generator of the present invention, a gas with hydrogen generated by an electrolytic cell is condensed and filtered out electrolytes with a condensate filter device, and then the gas with hydrogen is mixed with an atomizing gas generated by an atomizing device to generate a healthy gas for humans to breathe suitably. Furthermore, the gas generator of the present invention comprises a humidification device connected between the condensate filter device and the atomizing device, wherein the humidification device is used for further filtering out impurities in the gas with hydrogen to provide a more suitable healthy gas for humans to breathe.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
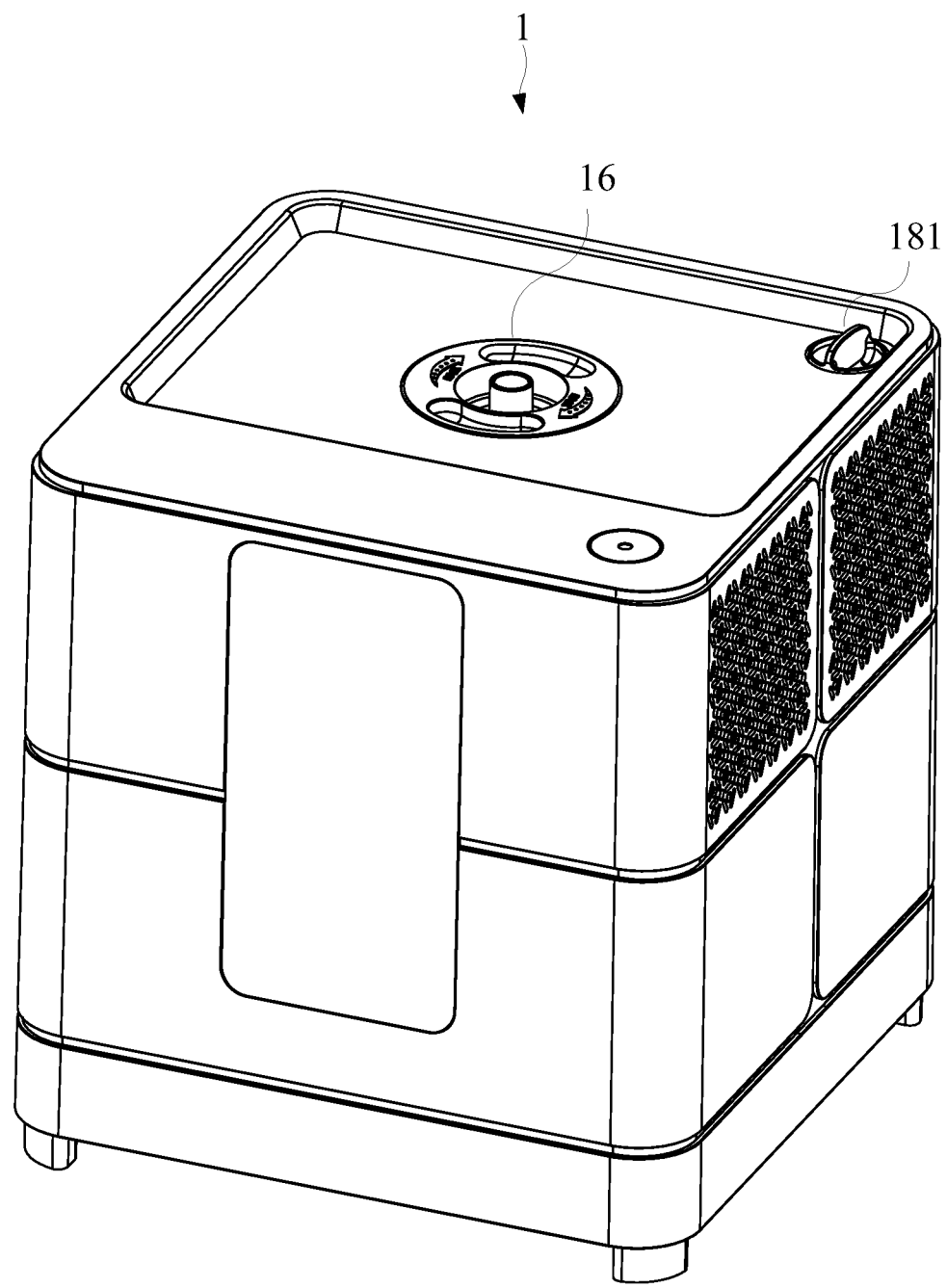
FIG. 1 shows a schematic diagram of the gas generator in one embodiment of the present invention.
Figure 2:
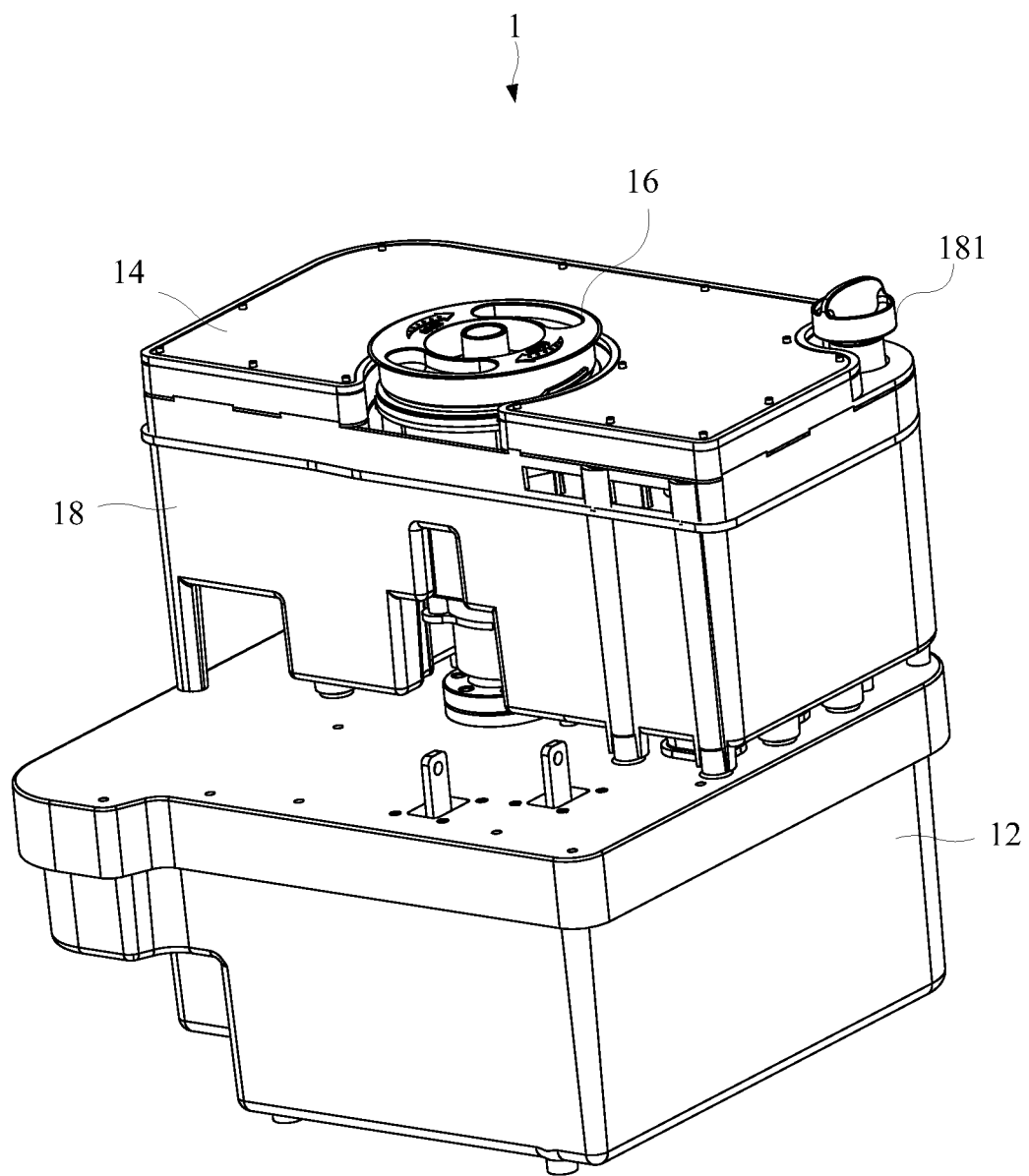
FIG. 2 shows a schematic diagram of the condensate filter device and the electrolytic cell of the gas generator in one embodiment of the present invention.
Figure 3:
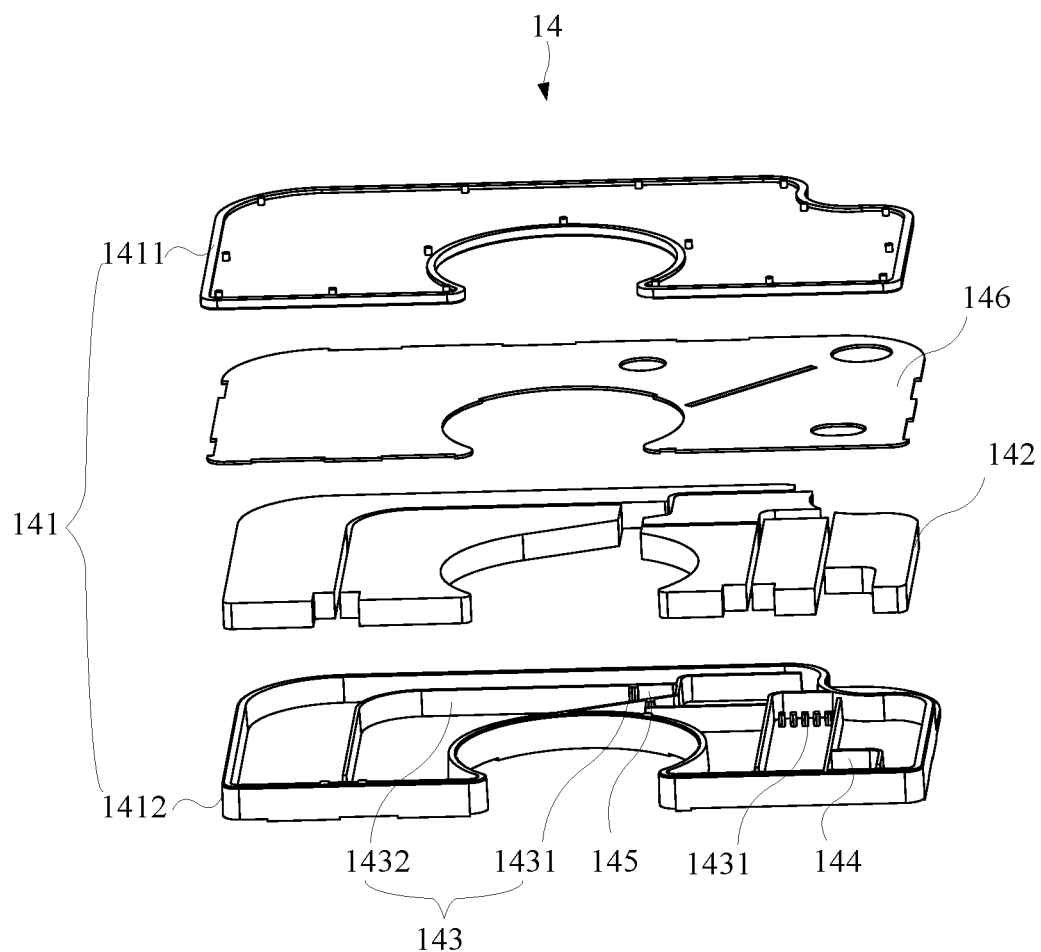
FIG. 3 shows an explosion diagram of the condensate filter device of the gas generator in one embodiment of the present invention.

Please refer to FIG. 1, FIG. 2, and FIG. 3. FIG. 1 shows a schematic diagram of the gas generator 1 in one embodiment of the present invention, FIG. 2 shows a schematic diagram of the condensate filter device 14 and the electrolytic cell 12 of the gas generator 1 in one embodiment of the present invention, and FIG. 3 shows an explosion diagram of the condensate filter device 14 of the gas generator 1 in one embodiment of the present invention. The gas generator 1 of the present invention comprises an electrolytic cell 12, a condensate filter device 14, and an atomizing device 16. The electrolytic cell 12 contains electrolyzed water, wherein the electrolyzed water comprises an electrolyte, and the electrolytic cell 12 is used for electrolyzing the electrolyzed water to generate a gas with hydrogen. The condensate filter device 14 comprises a gas pathway 141, a filter 142, and an isolated component 143. The gas pathway 141 is used for receiving the gas with hydrogen. The filter 142 is configured in the gas pathway 141 for filtering the gas with hydrogen to generate a filtered gas with hydrogen. The isolated component 143 is configured in the condensate filter device 14 for limiting the movement of the filter in the gas pathway. The atomizing device 16 is used for receiving the filtered gas with hydrogen, wherein the atomizing device 16 further generates an atomizing gas to be mixed with the filtered gas with hydrogen to generate a healthy gas. Additionally, the isolated component 143 can be an isolated cube 1431 or a pathway barrier sheet 1432.

Figure 4:
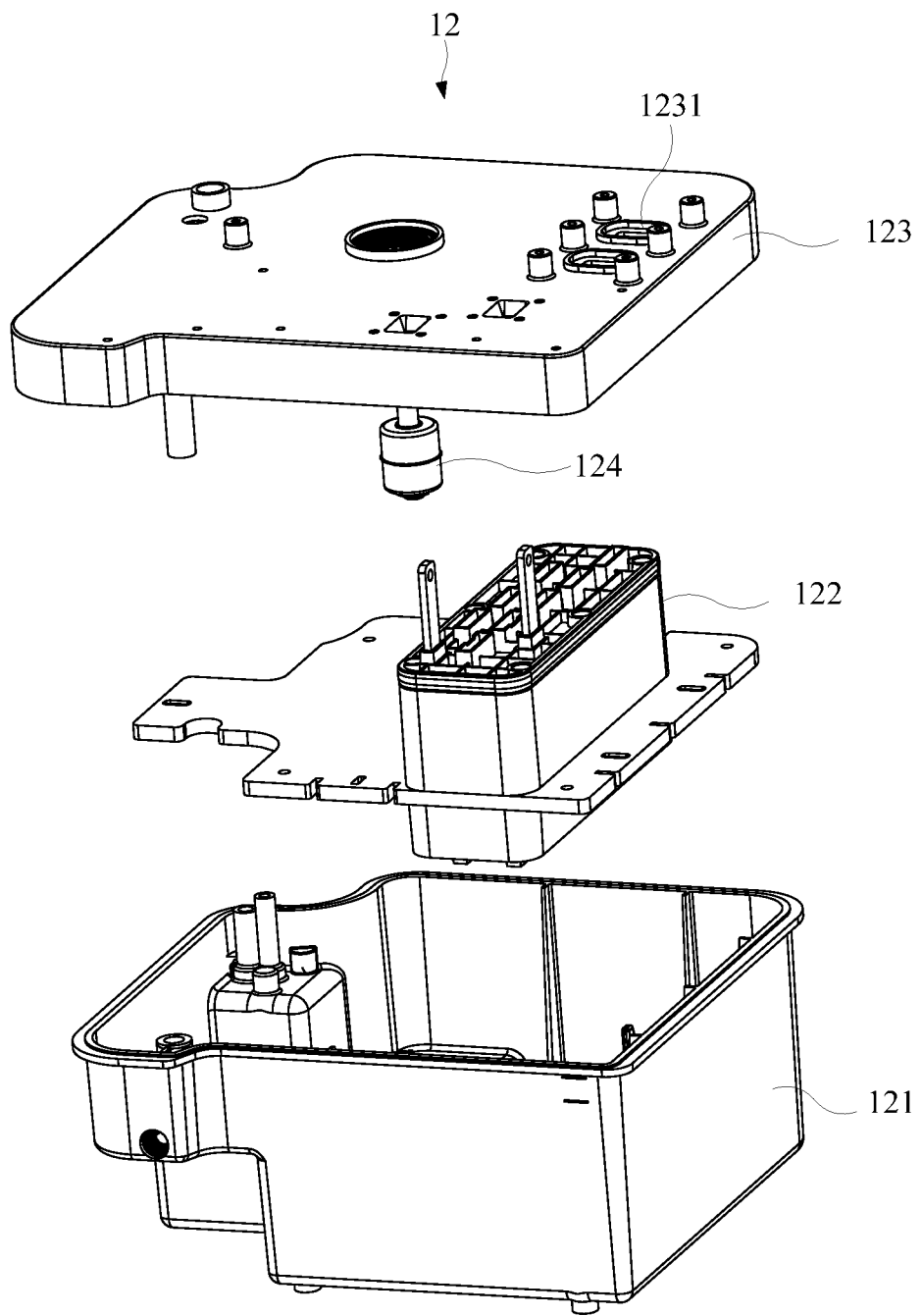
FIG. 4 shows an explosion diagram of the electrolytic cell of the gas generator in one embodiment of the present invention.

Please refer to FIG. 4, FIG. 4 shows an explosion diagram of the electrolytic cell 12 of the gas generator 1 in one embodiment of the present invention. The electrolytic cell 12 comprises a tank 121, an electrolysis device 122, and an upper cover of the electrolytic cell 123. The tank 121 contains electrolyzed water including an electrolyte, wherein the electrolyte can be, but not limited to, sodium hydroxide. In practical application, the electrolyte can be calcium carbonate or sodium chloride. Furthermore, the electrolyte can be a food grade of sodium hydroxide. The electrolysis device 122 is configured in the tank 121 for electrolyzing the electrolyzed water in the tank 121. Wherein, the electrolysis device 122 can be configured in the tank 121 by a fixed plate. The electrolysis device 122 can be assembled by a plurality of electrodes, and the plurality of electrodes are respectively disposed within the electrolysis device 122 at intervals to form a plurality of electrode channels for speeding up the generation of the gas with hydrogen by electrolyzing the electrolyzed water. The upper cover of the electrolytic cell 123 is configured on the tank 121 for separating the electrolyzed water from others. Wherein, the upper cover of the electrolytic cell 123 has an outlet of the electrolytic cell 1231 for outputting the gas with hydrogen generated by electrolyzing the electrolyzed water from the electrolytic cell 12.

In this embodiment, the electrolytic cell 12 can further comprises a water level meter 124 for detecting and alarming the remaining water level of the electrolyzed water in the tank 12 to avoid the danger of empty burning in the electrolytic cell 12.

Figure 5:
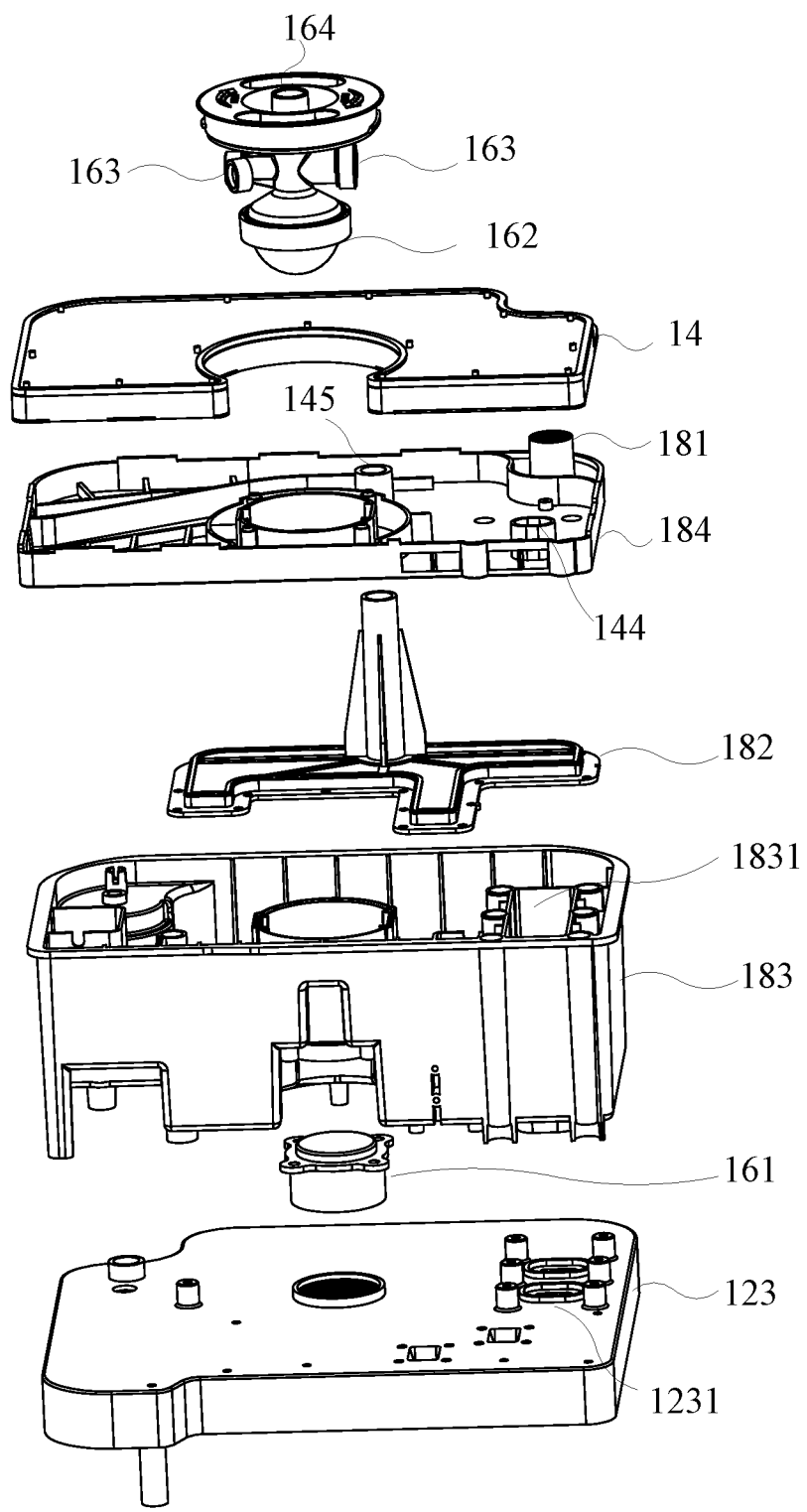
FIG. 5 shows an explosion diagram of devices above the electrolytic cell of the gas generator in one embodiment of the present invention.

Please refer to FIG. 5; FIG. 5 shows an explosion diagram of devices above the electrolytic cell 12 of the gas generator 1 in one embodiment of the present invention. The outlet of the electrolytic cell 1231 is connected to an electrolytic gas connecting channel 1831 above the outlet of the electrolytic cell 1231, wherein the electrolytic gas connecting channel 1831 is used for outputting the gas with hydrogen to the condensate filter device 14.

Please refer to FIG. 3 again; the condensate filter device 14 comprises a top cover of the gas pathway 1411 and a bottom cover of the gas pathway 1412. The top cover of the gas pathway 1411 is configured on the bottom cover of the gas pathway 1412, and the gas pathway 141 is formed when the top cover of the gas pathway 1411 is combined with the bottom cover of the gas pathway 1412.

The condensate filter device 14 has an inlet 144 and a vent 145, and the inlet 144 and the vent 145 are connected to the gas pathway 141 respectively. The gas with hydrogen enters the gas pathway 141 through the inlet 144. The vent 145 is used for outputting the filtered gas with hydrogen. The gas with hydrogen enters the inlet 144 through the electrolytic gas connecting channel 1831. The filter 142 configured in the gas pathway 141 filters out impurities in the gas with hydrogen to generate a filtered gas with hydrogen, and then the filtered gas with hydrogen flows out through the vent 145.

Wherein, one of the impurities filtered by the filter 142 is the electrolyte. Additionally, the filter 142 can be asbestos. Furthermore, the isolated component 143 is used for preventing the filter 142 from flowing into the inlet 144 or the vent 145 by limiting the movement of the filter 142 in the gas pathway 141. It should be understood that the word "limiting" of the present invention is not equal to "fixing", but reducing the degree of the filter 142 movement. In practical application, the filter 142 can comprises a plurality of filter films, and each filter film is limited by the isolated component 143. In this embodiment, the condensate filter device 14 comprises a condensate sheet 146 configured in the gas pathway 141 to further condense the gas with hydrogen flowing into the gas pathway 141.

Figure 6:
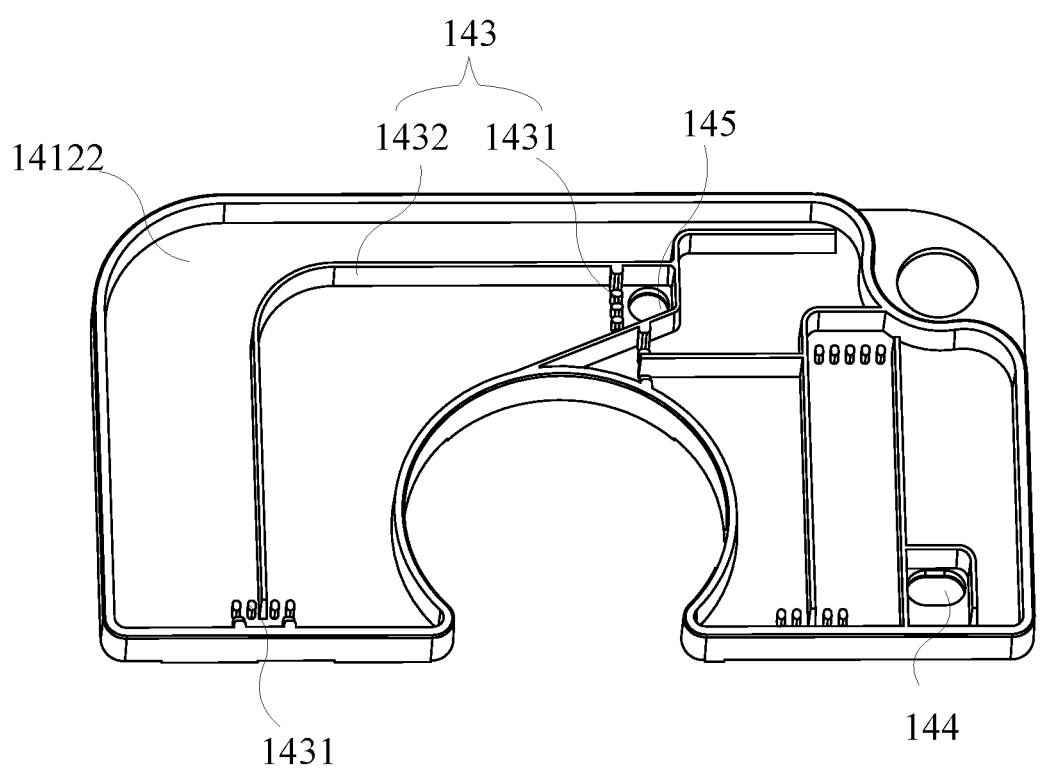
FIG. 6 shows a schematic diagram of the bottom cover of the gas pathway of the gas generator in one embodiment of the present invention.

Please refer to FIG. 6, FIG. 6 shows a schematic diagram of the bottom cover of the gas pathway 1412 of the gas generator 1 in one embodiment of the present invention. In this embodiment, the bottom cover of the gas pathway 1412 comprises a pathway substrate 14122, wherein the pathway barrier sheet 1432 is configured on the pathway substrate 14122. The gas pathway 141 meanderingly distributed over the condensate filter device 14 is formed when the top cover of the gas pathway 1411 is combined with the bottom cover of the gas pathway 1412. Furthermore, the pathway substrate 14122 and the isolated component 143 are formed integrally by one process.

Please refer to FIG. 5 again; the embodiment further comprises a humidification device 18 connected between the condensate filter device 14 and the atomizing device 16, wherein the humidification device 18 is used for further moisturizing and filtering the filtered gas with hydrogen received from the vent 145 and outputting the filtered gas with hydrogen to the atomizing device 16. Wherein, the humidification device 18 comprises a water-adding hole 181, a condensed gas connected channel 182, a humidification tank 183, and a top cover of the humidification tank 184, wherein a humidification space is formed when the humidification tank 183 is combined with the top cover of the humidification tank 184. The condensed gas connected channel 182 is connected between the vent 145 of the condensate filter device 14 and the humidification space for inputting the filtered gas with hydrogen to the humidification space. The water-adding hole 181 is used for adding a humidification liquid into the humidification space. Wherein, the outlet of the condensed gas connected channel can comprise a filter screen for further filtering and purifying the filtered gas with hydrogen.

The atomizing device 16 comprises an atomization oscillator 161, an atomization chamber 162, a filtered gas connected channel 163, and a healthy gas outlet 164. The atomization chamber 162 is used for containing an atomizing solution. The atomization oscillator 161 is used for transferring the atomizing solution in the atomization chamber 162 to an atomizing gas. The atomization chamber 162 is used for mixing the atomizing gas with the filtered gas with hydrogen entering from the filtered gas connected channel 163 to generate a healthy gas. Then the healthy gas outlet 164 outputs the healthy gas for a user to use. The atomizing gas can be selected from a group comprising water vapor, an atomizing solution, a volatile essential oil, and any combination thereof. Furthermore, the atomizing device 16 can comprise a gas flow valve to adjust the amount of the outputted healthy gas so that the user can adjust the intake.

To summarize the statement mentioned above, the priority of the present invention is to provide a gas generator. In the gas generator of the present invention, a gas with hydrogen generated by an electrolytic cell is condensed and filtered out electrolytes by a condensate filter device, and then the gas with hydrogen is mixed with an atomizing gas generated by an atomizing device to generate a healthy gas for human to breathe suitably. Furthermore, the gas generator of the present invention comprises a humidification device connected between the condensate filter device and the atomizing device, wherein the humidification device is used for further filtering out impurities in the gas with hydrogen to provide a more suitable healthy gas for humans to breathe.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
a water tank having a first hollow portion for containing electrolyzed water;
an electrolytic device disposing in the first hollow portion to electrolyze the electrolyzed water to generate a gas with hydrogen to the water tank;
a condensate filter device configured for filtering out impurities in the gas with hydrogen to generate a filtered gas with hydrogen;
a humidification device having a humidification tank and a top cover, wherein a humidification space is formed between the humidification tank and the top cover; and
an electrolytic gas connecting channel integrated into the humidification tank and separated from the humidification space;
wherein the electrolytic gas connecting channel is connected to the water tank and the condensate filter device to pass the gas with hydrogen from the water tank to the condensate filter device, and the humidification space is configured to contain a humidification liquid to humidify the filter gas with hydrogen.

2. The gas generator of claim 1, wherein the humidification device further comprises a condensed gas connected channel coupled to the condensate filter device to receive the filter gas with hydrogen, and one end of the condensed gas connected channel inputs the filter gas with hydrogen into the humidification space.

3. The gas generator of claim 1, further comprising an atomizing device configured for generating an atomizing gas to be mixed with the filtered gas with hydrogen, wherein a portion of the atomizing device is accommodated in a space integrated into the humidification tank and separated from the humidification space.

4. A gas generator, comprising:
a water tank having a first hollow portion for containing electrolyzed water;
an electrolytic device disposing in the first hollow portion for electrolyzing the electrolyzed water to generate a gas with hydrogen to the water tank;
a condensate filter device vertically stacking above the water tank for filtering out impurities in the gas with hydrogen to generate a filtered gas with hydrogen;
a humidification device vertically stacking above the water tank for humidifying the filtered gas with hydrogen to generate a humidified gas with hydrogen; and
an atomizing device configured for generating an atomizing gas to be mixed with the humidified gas with hydrogen;
wherein a portion of the atomizing device is accommodated in a space integrated into the humidification device.

5. The gas generator of claim 4, wherein the humidification device has a humidification tank and a top cover, and the humidification tank is vertically separated from the water tank.

6. The gas generator of claim 5, wherein the condensate filter device is stacked on the top cover of the humidification device and is vertically separated from the humidification tank of the humidification device.

7. The gas generator of claim 4, further comprising an upper cover configured on the water tank, wherein the upper cover separates the water tank from the condensate filter device and the humidification device.

8. The gas generator of claim 7, wherein the upper cover has a plurality of positioning pillars, and the humidification device has a humidification tank which comprises a plurality of positioning holes, wherein the humidification device is stacked on the upper cover by coupling the plurality of positioning holes to the plurality of positioning pillars.

9. A gas generator, comprising:
a water tank having a first hollow portion for containing electrolyzed water and an upper cover configured on the water tank;
an electrolytic device disposing in the first hollow portion for electrolyzing the electrolyzed water to generate a gas with hydrogen to the water tank;
a condensate filter device vertically stacking above the water tank for filtering out impurities in the gas with hydrogen to generate a filtered gas with hydrogen; and
a humidification device vertically stacking above the water tank to receive and humidify the filtered gas with hydrogen;
wherein a plurality of electrodes are respectively disposed in the electrolytic device at intervals to form a plurality of electrode channels, and the electrolytic device is configured in the water tank by a fixed plate, wherein the fixed plate extends from sidewalls of the electrolytic device and divides the first hollow portion of the water tank into an upper hollow space and a lower hollow space.

10. The gas generator of claim 9, further comprising an atomizing device configured for generating an atomizing gas to be mixed with the filtered gas with hydrogen, wherein the atomizing device comprises an atomization chamber, a filtered gas connected channel and a healthy gas outlet, the atomization chamber is used for mixing the atomizing gas with the filtered gas with hydrogen entering from the filtered gas connected channel to generate a healthy gas.

11. The gas generator of claim 9, further comprising an atomizing device configured for generating an atomizing gas to be mixed with the filtered gas with hydrogen, wherein the humidification device has a humidification tank, and a space is integrated into the humidification tank for accommodating a first portion of the atomizing device.

12. The gas generator of claim 11, wherein the condensate filter device encompasses a second portion of the atomizing device.

* * * * *